(12) United States Patent
Hii

(10) Patent No.: US 7,232,923 B2
(45) Date of Patent: Jun. 19, 2007

(54) METHOD OF HYDROAMINATING N-ALKENOYLCARBAMATES WITH PRIMARY AROMATIC AMINES

(75) Inventor: King Kuok (Mimi) Hii, London (GB)

(73) Assignee: Imperial Innovations Limited (GB)

( * ) Notice: Subject to any disclaimer, the term of this patent is extended or adjusted under 35 U.S.C. 154(b) by 95 days.

(21) Appl. No.: 11/057,149

(22) Filed: Feb. 15, 2005

(65) Prior Publication Data

US 2006/0183933 A1 Aug. 17, 2006

(51) Int. Cl.
*C07C 269/04* (2006.01)
(52) U.S. Cl. .............................. 560/24; 564/59; 564/86; 564/152; 558/410
(58) Field of Classification Search .................. 564/59, 564/86, 152; 558/410; 560/24, 27
See application file for complete search history.

(56) References Cited

U.S. PATENT DOCUMENTS 6,605,708 B1 8/2003 Habus et al.

OTHER PUBLICATIONS

Li et al, Eur. J. Org. Chem., 959-964 (Feb. 16, 2004).
Hii, KK, "Developing Novel Catalytic Systems—Addition of Amines to Double Bonds", Details of Grant, GR/R50332/01, 1 page, Feb. 2002.
Li, K. et al., "Dicationic [BINAP)Pd(solvent$_2$)]$^{2+}$[TfO]$_2$: enantioselective hydroamination catalyst for alkenoyl-*N*-oxazolidinones", *Communication*, Apr. 8, 2003, www.rsc.org/chemcomm, 2 pages.

*Primary Examiner*—Shailendra Kumar
(74) *Attorney, Agent, or Firm*—Wilmer Cutler Pickering Hale and Dorr LLP

(57) ABSTRACT

The invention provides methods for hydroaminating N-alkenoyl carbamates with aromatic amines.

13 Claims, 1 Drawing Sheet

METHOD OF HYDROAMINATING N-ALKENOYLCARBAMATES WITH PRIMARY AROMATIC AMINES

FIELD OF THE INVENTION

The invention relates to methods of hydroaminating N-alkenoyl carbamates with aromatic amines.

BACKGROUND OF THE INVENTION

The hydroamination (HA) reaction involves the addition of an N—H bond across a double or triple bond, furnishing valuable nitrogen containing molecules from readily available and non-hazardous precursors with 100% atom economy, making it one of the most desirable processes, economically and environmentally. Alkenes containing electron withdrawing substituents are more susceptible to nucleophilic attack by alkyl amines, and these so called aza-Michael addition reactions may occur in the absence of catalysts. However, in many cases the reaction has an unfavourable $\Delta G^0$ and gave poor yields even at extremely high reaction temperatures and pressures.

Very few catalysts can facilitate the addition of N—H to double bonds (hydroamination/aza-Michael addition reaction) with high enantioselectivity. Prior to the current invention, only three late transition metal catalysts are known to generate ee values of $\geq 90\%$. These are an iridium-fluoride system which promotes the addition of aniline to norbonene (24%, 91% ee), palladium-catalysed addition of primary aromatic amines to 1,3-dienes (up to 95% ee) and nickel-catalysed addition of secondary aromatic amines to alkenoyl-N-oxazolidinones (up to 90% ee). In the examples using palladium or nickel catalysed reactions, catalyst loadings of 5 mol % were employed at room temperature, but reaction times of between 40 h to 5 days were required to achieve significant yields.

The enantioselective addition of primary and secondary aromatic amines to alkenoyl-N-oxazolidinones, catalysed by the cationic palladium complex $[(R\text{-BINAP})Pd(\text{solvate})_2]^{2+}$ $[TfO]^-_2$, with ee's up to 93%, has recently been reported. It is postulated that the observed addition occurs via a catalytic intermediate as illustrated below

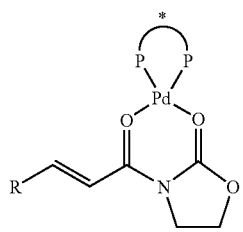

wherein activation of the unsaturated double bond occurs due to the chelation of oxazolidinone functionality to the metal centre. Formation of the catalytic intermediate is favoured due to the sterically hindered conformation of the alkenoyl-N-oxazolidinone. Both ketone functionalities are held in the correct orientation to interact with the palladium metal, thereby facilitating the formation of the catalytic intermediate and ultimately the enantiomerically selective addition of the aromatic amine to the alkenoyl-N-oxazolidinone.

While the use of the alkenoyl-N-oxazolidinones provides a useful route to such important compounds as beta amino acids and derivatives thereof, the use of such sterically hindered oxazolidinones is not always desirable or practicable. There is therefore a need in the art for a process for the hydroamination of less sterically hindered alkenes.

SUMMARY OF THE INVENTION

The invention provides a process for hydroaminating N-alkenoyl carbamates with aromatic amines. The hydroaminated N-alkenoyl carbamates can be used as precursors to β amino acids, amide derivatives, and other important compounds.

BRIEF DESCRIPTION OF THE DRAWINGS

Then invention may be put into practice in various ways and a number of specific embodiments will be described by way of example to illustrate the invention with reference to the accompanying drawings in which.

DETAILED DESCRIPTION OF THE INVENTION

Figure 1:
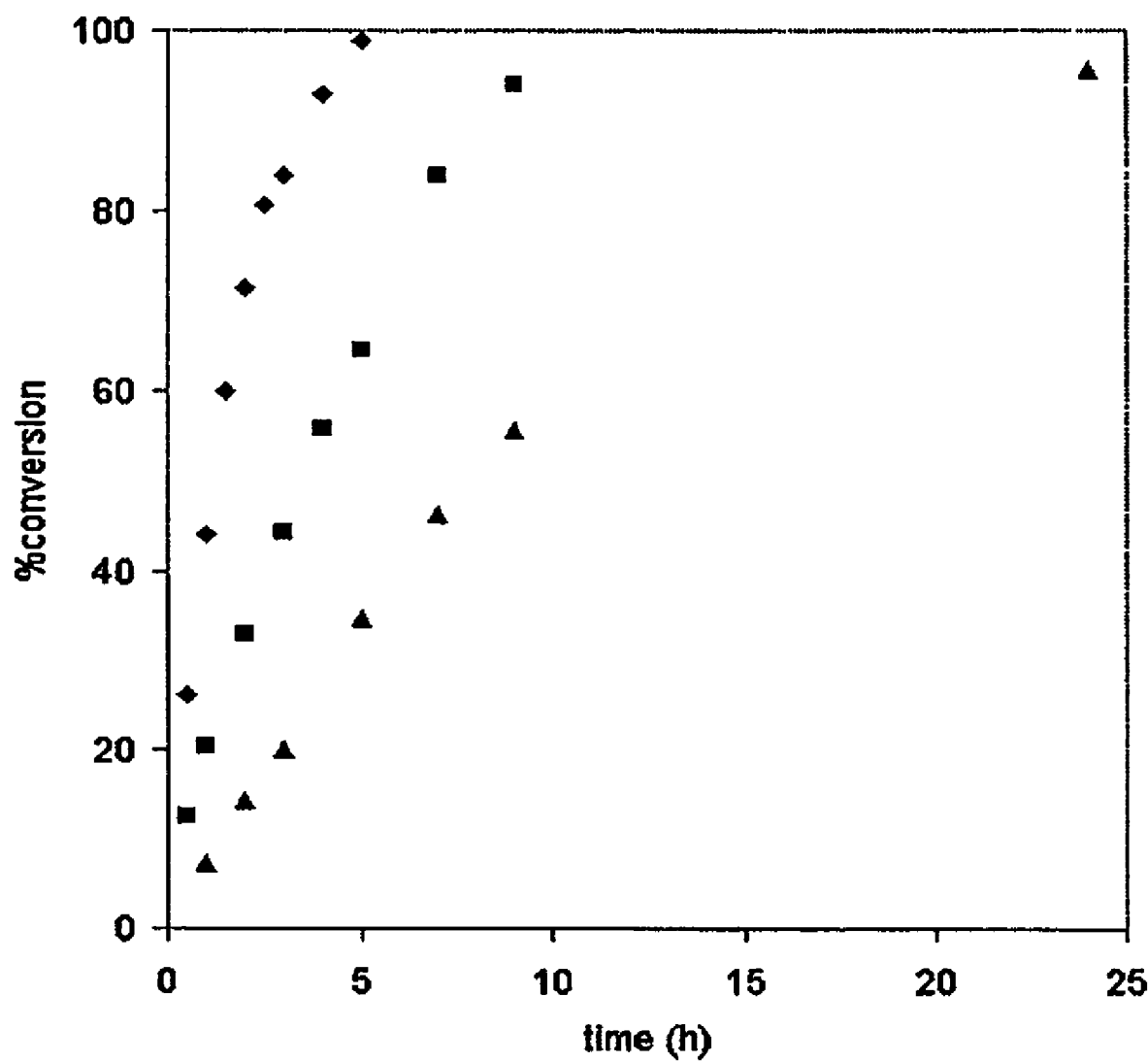
FIG. 1 shows the rate of catalysed addition of p-chloroaniline (diamonds), aniline (squares) and p-anisidine (triangles) to tert-butyl N-butenoyl-carbamate, 2a, monitored using $^1$H NMR spectroscopy.

The first aspect of the invention provides a process for forming a compound of formula I

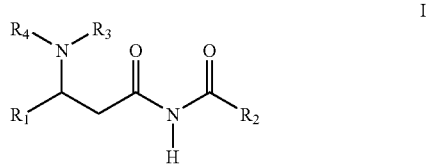

comprising reacting a compound of formula II

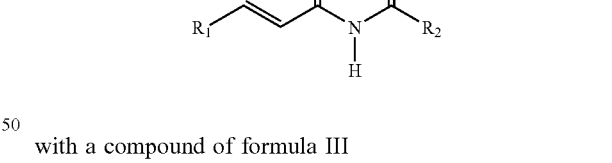

with a compound of formula III

in the presence of the catalyst $[(R\text{-BINAP})Pd(\text{solvent})_2]^{2+}$ $[TfO]^-_2$.

The identity of $R_1$ is not limited and can be any group. For example, $R_1$ may be a chemical moiety such as a peptide, amino acid, dipeptide, a sugar, or a polymer. $R_1$ may alternatively be selected from hydrogen, $C_{1-12}$ alkyl, $C_{2-12}$ alkenyl, $C_{2-12}$ alkynyl, $C_{3-12}$ aryl or $C_{3-12}$ heterocyclyl, optionally substituted by one or more of $C_{1-6}$ alkyl, halogen, $C_{1-6}$ haloalkyl, $OR_5$, $SR_5$, $NO_2$, $CN$, $NR_5R_5$, $NR_5COR_5$, $NR_5CONR_5R_5$, $NR_5COR_5$, $NR_5CO_2R_5$, $CO_2R_5$, $COR_5$, $CONR_{52}$, $S(O)_2R_5$, $SONR_{52}$, $S(O)R_5$, $SO_2NR_5R_5$, $NR_5S(O)_2R_5$, wherein each $R_5$ may be the same or different and is hydrogen, $C_{1-6}$ alkyl, $C_{1-6}$ haloalkyl or $C_{6-12}$ aryl;

$R_2$ is hydrogen, $C_{1-12}$ alkyl wherein the $C_{1-12}$ alkyl group optionally incorporates one or two insertions selected from the group consisting of —O—, —N($R_5$)—, —S(O)— and —S($O_2$)—, or aryl or with the adjacent carboxyl group forms an amino protecting group such as a carbamate including benzyloxycarbonyl, t-butoxycarbonyl, 2-(4-biphenylyl)-isopropoxycarbonyl, 9-fluorenylmethoxycarbonyl, wherein said alkyl or aryl group can be optionally substituted with one or more of those groups described for $R_1$.

$R_3$ is hydrogen or $C_{1-12}$ alkyl.

$R_4$ is aryl or heterocycyl wherein said aryl or heteroaryl group can be optionally substituted with one or more of those groups described for $R_1$ $R_1$ is preferably a $C_{1-10}$ alkyl group such as methyl, ethyl, or n-propyl.

Preferably $R_2$ is $OCH_3$ or $OC(CH_3)_3$.

$R_3$ is preferably H.

$R_4$ is preferably

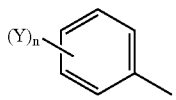

wherein Y is H, halogen, $C_{1-6}$ alkyl or $OC_{1-6}$ alkyl, and n is 1 to 5, preferably 1, 2 or 3. More preferably Y is H, Cl, methyl or O-methyl. The Y group may be in the ortho, meta or para position, preferably the para position.

In a preferred embodiment, the catalyst is provided at less than 5 mol % catalyst, for example 0.5 mol %, 1 mol %, 2 mol %, 3 mol % or 4 mol %. The catalyst is preferably provided in the range 2–5 mol %. This level of catalyst is less than previously reported, which has both economical and environmental advantages. As less catalyst is required, the process is cheaper, and produces less waste palladium that needs to be disposed of safely.

The process produces enantiomeric excesses greater than 99% (see Table 1). The process of the present application therefore produces an improved method of conjugate additions with significant improvements in obtained enantiomeric excesses.

The catalyst, $[(R\text{-}BINAP)Pd(solvent)_2]^{2+}[TfO]^-_2$ preferably has the following formula:

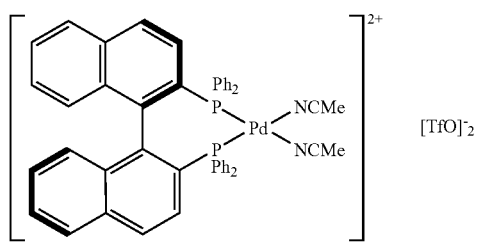

Suitable solvents include dichloromethane, toluene and acetonitrile.

For the purposes of all aspects of this invention, alkyl relates to both straight chain and branched alkyl radicals of 1 to 12 carbon atoms, preferably 1 to 8 carbon atoms and most preferably 1 to 4 carbon atoms including but not limited to methyl, ethyl, n-propyl, isopropyl, n-butyl, sec-butyl, isobutyl, tert-butyl n-pentyl, n-hexyl, n-heptyl, n-octyl. In particular, alkyl relates to a group having 1, 2, 3, 4, 5, 6, 7, 8, 9, 10, 11 or 12 carbon atoms. The term alkyl also encompasses cycloalkyl radicals including but not limited to cyclopropyl, cyclobutyl, $CH_2$-cyclopropyl, $CH_2$-cyclobutyl, cyclopentyl or cyclohexyl. In particular, cycloalkyl relates to a group having 3, 4, 5, 6, 7, 8, 9, 10, 11 or 12 carbon atoms. Cycloalkyl groups may be optionally substituted or fused to one or more carbocyclyl or heterocyclyl group. Haloalkyl relates to an alkyl radical as defined above preferably having 1 to 8 carbon atoms, preferably 1 to 4 carbon atoms substituted with one or more halide atoms for example one or more of F, Cl, Br or I, such as $CH_2CH_2Br$, $CF_3$ or $CCl_3$.

The term "alkenyl" means a straight chain or branched alkylenyl radical of 2 to 12 carbon atoms, preferably 2 to 6 carbon atoms and most preferably 2 to 4 carbon atoms, and containing one or more carbon-carbon double bonds and includes but is not limited to ethylene, n-propyl-1-ene, n-propyl-2-ene, isopropylene, etc. In particular, alkenyl relates to a group having 2, 3, 4, 5, 6, 7, 8, 9, 10, 11 or 12 carbon atoms. The term "alkynyl" means a straight chain or branched alkynyl radical of 2 to 12 carbon atoms, preferably 2 to 6 carbon atoms and most preferably 2 to 4 carbon atoms, and containing one or more carbon-carbon triple bonds and includes but is not limited to ethynyl, 2-methylethynyl etc. In particular, alkynyl relates to a group having 2, 3, 4, 5, 6, 7, 8, 9, 10, 11 or 12 carbon atoms.

"Aryl" means an aromatic 3–12 membered hydrocarbon preferably a 6–12 membered hydrocarbon containing one ring or being fused to one or more saturated or unsaturated rings including but not limited to phenyl, napthyl, anthracenyl or phenanthracenyl.

"Heterocyclyl" means a 3–12 membered ring system preferably a 5–12 membered aryl containing one or more heteroatoms selected from N, O or S and includes heteroaryl. In particular, the terms "aryl", "heteroaryl" and "heterocycyl" relate to a group having 3, 4, 5, 6, 7, 8, 9, 10, 11 or 12 carbon atoms.

The heterocyclyl system can contain one ring or may be fused to one or more saturated or unsaturated rings; the heterocyclyl can be fully saturated, partially saturated or unsaturated and includes but is not limited to heteroaryl and heterocarbocyclyl. Examples of carbocyclyl or heterocyclyl groups include but are not limited to cyclohexyl, phenyl, acridine, benzimidazole, benzofuran, benzothiophene, benzoxazole, benzothiazole, carbazole, cinnoline, dioxin, dioxane, dioxolane, dithiane, dithiazine, dithiazole, dithiolane, furan, imidazole, imidazoline, imidazolidine, indole, indoline, indolizine, indazole, isoindole, isoquinoline, isoxazole, isothiazole, morpholine, napthyridine, oxazole, oxadiazole, oxathiazole, oxathiazolidine, oxazine, oxadiazine, phenazine, phenothiazine, phenoxazine, phthalazine, piperazine, piperidine, pteridine, purine, pyran, pyrazine, pyrazole, pyrazoline, pyrazolidine, pyridazine, pyridine, pyrimidine, pyrrole, pyrrolidine, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, or trithiane.

For the purpose of the present invention, the term "fused" includes a polycyclic compound in which one ring contains one or more atoms preferably one, two or three atoms in common with one or more other ring.

Halogen means F, Cl, Br or I, preferably Br and F.

The process of the present invention allows non-cyclic amino protecting groups, such as t-Boc, to be used in the reaction under mild conditions resulting in unprecedently high turnovers and enantioselectivities. Furthermore such non-cyclic protecting groups can be removed under mild basic (e.g. NaOH) or acidic (e.g. trifluoroacetic acid, TFA) conditions to produce valuable optically active β-amino acids, amide derivatives, or other useful compounds. The ability to produce β-amino acids and amides represents another advantage over the process using alkenoyl-N-oxazolidinones.

Thus in a preferred embodiment the process further comprises the step of:
(a) transforming the compound of Formula I under mild basic conditions to a β-amino acid; or
(b) transforming the compound of Formula I under mild acidic conditions to a β-amino amide.

For the purposes of this invention, a mild acid or base is one which will not lead to the racemisation of the newly created stereogenic centre. The acid/or base is preferably used at room temperature. Concentrations are between 0.1M and 10M. The procedure is dependent on the nature of the $R_2$ group. Transformation into an acid can be carried out by hydrolysis with NaOH or $Ba(OH)_2$ or HCl in $H_2O$ or MeOH.

Transformation to an amide can be carried out according to procedures known in the art. For example when $R_2$ is tert-butyl, removal of $R_2$ is carried out with HCl/dioxane, or $TFA/CH_2Cl_2$, or HBr/AcOH, or zeolites; when $R_2$ is fluorenyl, removal of $R_2$ is carried out with any secondary or tertiary nitrogen base (e.g. triethylamine, piperidine, DBU); when $R_2$ is benzyl, removal of $R_2$ is carried out by any hydrogenation procedure (e.g. $H_2$, Pd/C); ammonia/MeOH when $R_2$ is Me, removal of $R_2$ is carried out with ammonia/MeOH

EXAMPLES

The invention will now be described with reference to one or more of the following non-limiting examples.

Manipulations were performed using standard Schlenk techniques under inert atmosphere of $N_2$ or Ar. Dichloromethane, toluene and acetonitrile solvents were dried over $CaH_2$, distilled and stored under a nitrogen atmosphere prior to use. Column chromatography was performed on silica gel (Kieselgel 60, 63–200 μm). NMR spectra were recorded on Bruker Avance 360 ($^1H$ and $^{13}C$ at 360 and 90.6 MHz respectively) or 400 ($^1H$ and $^{13}C$ at 400 and 100.6 MHz respectively) instruments. Chemical shifts are reported in δ (ppm), referenced to residual signals of deuterated chloroform. Optical rotation values were measured on a Perkin Elmer polarimeter 343 using a 10 cm solution cell, concentration of the samples was indicated as g/mL, given in the parenthesis. Melting points (uncorrected) were determined on an Electrothermal Gallenhamp apparatus. Elemental analytical service was provided by London Metropolitan University. Mass spectra (MS) were recorded using Electron Impact (EI, low and high resolution) or Electrospray (ES, high resolution) techniques. HPLC analyses were performed on a Gilson HPLC system using Daicel Chiralpak AD or AS columns (equipped with an autoinjector with a 20 μl loop). Detection was made by UV absorption at 215 nm. Acid chlorides were prepared from the appropriate acid by chlorination (thionyl chloride). Unless otherwise indicated, all chemicals were obtained commercially and used as received. Preparation of complex 1 has been previously reported (Li et al, 2003).

The process of the present invention can be carried out as shown in Scheme 1, which shows the conjugate addition of anilines to tert-butyl N-alkenoyl carbamates.

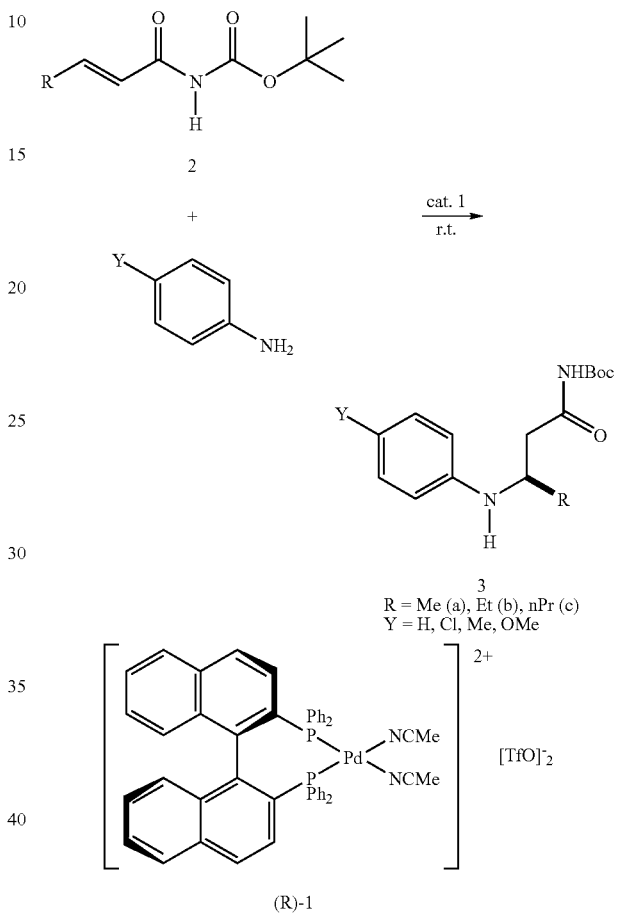

The addition of aniline to N-butenoyl-tert-butyl-carbamate 2a was initially examined. Using 5 mol % of complex 1 as the catalyst, reactions proceeded cleanly at room temperature in toluene, to furnish product 3a quantitatively in 18 h with high enantiomeric excess (97% ee, entry 1). Presumably, due to competitive coordination of the solvent to the cationic metal centre, the rate of the reaction was retarded when dichloromethane was employed as the solvent, accompanied by a slight lost of ee (entry 2). More significantly, quantitative conversions were obtained within 40 h when the catalytic loading is reduced to 2 mol %, with only a slight erosion on the stereoselectivity (entry 3).

The addition of p-chloroaniline to 2a proceeded with perfect enantioselectivity (>99% ee, entry 4) and also with the quickest turnover. In this instance, catalyst loading may be reduced to 2 mol %, without affecting the yield or selectivity (entry 5). The addition of p-toluidine proceeded with yield and ee value similar to that of aniline (entry 6), but the addition of p-anisidine achieved the same number of turnovers only after 40 h, with moderate ee of 73% (entry 7).

Previously, the addition of nitrogen nucleophiles to activated olefins, such as alkenoyl-N-oxazolidinones, are often thought to proceed via a Lewis acid-promoted process, where the attack of the weak nucleophile was facilitated by chelation of the oxazolidinone functionality to a cationic metal centre. It was found that the relative rates of addition of amines to the N-alkenoyl carbamate 2a increase in the order p-anisidine<aniline<p-chloroaniline (FIG. 1), i.e. the least nucleophilic amine is, in fact, the most reactive. What we have observed in the present system clearly contradicts the earlier hypothesis, thus indicating the operation of either a competitive rate-determining step, or an entirely different reaction mechanism.

At 5 mol % catalyst loading, the addition of p-chloroaniline was essentially complete within 5 hours. Corresponding to a turnover rate of 4 h$^{-1}$, this is not only the most selective, but also, by far, the most active late transition metal-catalysed system. Concurrently, the ee's of the products were monitored by chiral HPLC, which showed that enantioselectivity was established at the onset and remained constant during the course of the reactions.

Homologation of the β-substituent to N-pentenoyl and hexenoyl carbamates (2b and 2c) decelerated the rate of the conjugate addition (entries 8–15). The unusually long reaction time required for the addition of p-toluidine to 2b (entry 10), compared to the addition of other amines (entries 8, 9 and 11), is also an interesting feature, which suggests the possibility of competitive rate determining steps. Nevertheless, good to excellent conversion and yield of products were obtained, and the enantioselectivity remained high in most cases, except the addition of p-anisidine, which proceeded with low selectivities (entries 11 and 15).

The bulky NHBoc group appeared to play no part in the outcome of the reaction, as shown by the addition of aniline to the methyl carbamate 4 (Scheme 2), which also proceeded in high yield (95%) and enantioselectivity (92% ee).

Scheme 2.

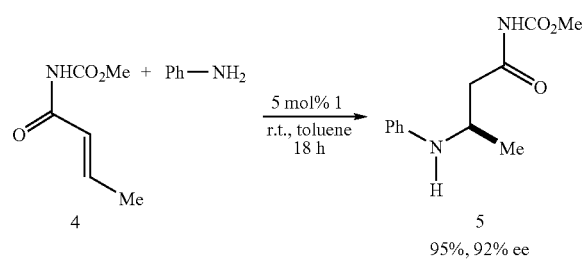

The NHBoc functionality may be easily transformed under mild basic or acidic conditions to afford valuable optically active β-amino acid or amide derivatives. Hence, 3a was converted quantitatively into the corresponding β-amino acid or amide derivatives 6 and 7, respectively (Scheme 3). N-Aryl-β-amino acids have been prepared previously by Pd/Cu-catalysed aryl amination of β-amino acids with aryl halides. The absolute stereochemistry of 6 (and 7) was thus established to be (S), by comparison of its optical rotation with that reported.

Scheme 3.

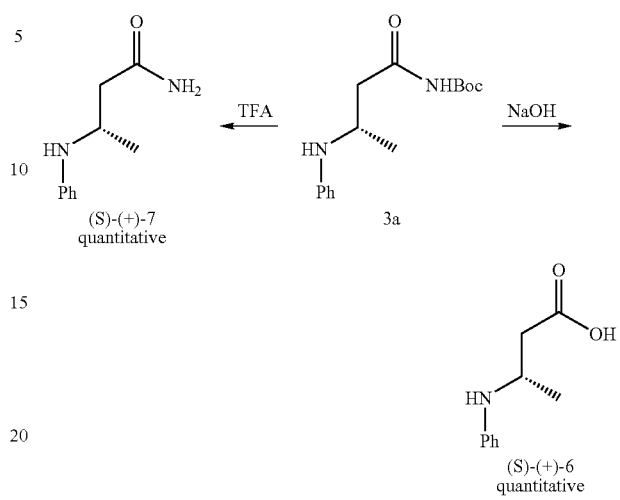

Typical procedure for the synthesis of tert-butyl alkenoylcarbamate:

tert-Butyl (2E)-but-2-enoylcarbamate (2a): To a solution of tert-butyl carbamate (1.0 g, 8.54 mmol) in THF (20 mL) at −78° C., were added nBuLi and 2-butenoyl chloride successively, in the following quantities (nBuLi/2-butenoyl chloride): 5.34/0.41, 2.67/0.21, 1.34/0.10, 0.67/0.05, 0.34/0.03 mL. Stirring was continued for 30 min, before the reaction mixture was poured into an ice-cooled solution of saturated aq. NaHCO$_3$ (50 mL) and extracted with EtOAc. The combined organic layers were washed with brine, dried over MgSO$_4$, and evaporated. The crude product was purified by flash chromatography (Et$_2$O:pet. ether, 1:3, R$_f$ 0.4) to give the product as a white solid. Yield 81% (1.28 g). m.pt. 138–139° C. $^1$H NMR: δ 1.49 (s, 9H, tBu); 1.92 (dd, 1H, CH$_3$CH, $^2J_{HH}$=6.8 Hz, $^3J_{HH}$=1.5 Hz); 6.82 (dd, 1H, COCH, $^2J_{HH}$=15.2 Hz, $^3J_{HH}$=1.5 Hz); 7.05–7.15 (m, 1H, CH$_3$CH); 7.31 (s, br, 1H, NH). $^{13}$C NMR: δ 15.9 (CH$_3$CH), 27.9 (C(CH$_3$)$_3$), 82.3 (C(CH$_3$)$_3$), 121.2 (COCH), 145.5 (CH$_3$CH), 150.5(CO$_2$), 166.3 (COCH). m/z (HR-ESMS): Expected 185.1052 (M$^+$), observed 185.1046. Anal. calcd for C$_9$H$_{15}$NO$_3$: C, 58.36; H, 8.16; N, 7.56%. Found: C, 58.08; H, 8.05; N, 7.63%.

tert-Butyl (2E)-pent-2-enoylcarbamate (2b): White solid (Et$_2$O:pet, ether, 1:3, R$_f$ 0.4). Yield 70% (1.19 g). m.pt. 78–79° C. $^1$H NMR: δ 1.09 (t, 3H, CH$_3$CH$_2$, $^2J_{HH}$=7.4 Hz); 1.47 (s, 9H, tBu); 2.23–2.31 (m, 2H, CH$_3$CH$_2$); 6.79 (d, 1H, COCH, $^2J_{HH}$=15.6 Hz); 7.11–7.19 (m, 1H, CH$_2$CH); 7.31 (s, br, 1H, NH). $^{13}$C NMR: δ 12.1 (CH$_3$CH$_2$), 25.7 (CH$_3$CH$_2$), 28.0 (C(CH$_3$)$_3$), 82.4 (C(CH$_3$)$_3$), 120.7 (COCH), 150.5 (CH$_3$CH), 152.1 (CO$_2$), 166.3 (COCH). m/z (HR-ESMS) Expected 199.1208 (M$^+$), observed 199.1203. Anal. calcd for C$_{10}$H$_{17}$NO$_3$: C, 60.28; H, 8.60; N, 7.03%. Found: C, 60.42; H, 8.75; N, 6.85%.

tert-Butyl (2E)-hex-2-enoylcarbamate (2c): White solid (Et$_2$O:pet. ether, 1:3, R$_f$ 0.4). Yield 80% (1.46 g). m.pt.

71–72° C. $^1$H NMR: δ 0.93 (t, 3H, CH$_3$CH$_2$, $^2J_{HH}$=7.3 Hz); 1.45–1.55 (m, 2H, CH$_3$CH$_2$); 1.49 (s, 9H, tBu); 2.20–2.26 (m, 2H, CH$_3$CH$_2$CH$_2$); 6.79 (d, 1H, COCH, $^2J_{HH}$=15.4 Hz); 7.06–7.14 (m, 1H, CH$_2$CH); 7.36 (s, br, 1H, NH). $^{13}$C NMR: δ 13.7 (CH$_3$CH$_2$), 21.3 (CH$_3$CH$_2$), 28.0 (C(CH$_3$)$_3$), 34.6 (CH$_2$CH), 82.4 121.6 (COCH), 150.5 (CH$_3$CH), 150.7 (CO$_2$), 166.2 (COCH). m/z (HR-ESMS) Expected 213.1365 (M$^+$), observed 213.1359. Anal. calcd for C$_{11}$H$_{19}$NO$_3$: C, 61.95; H, 8.98; N, 6.57%. Found: C, 62.24; H, 8.93; N, 6.37%.

Typical catalytic procedure: 0.022 g (0.020 mmol) of complex 1 and tert-butyl alkenoylcarbamate (0.60 mmol) were placed in a thick-walled Young's tube. A solution of the corresponding amine (0.40 mmol) in 2.0 mL of toluene was then added via syringe. The Young's tube was sealed (PTFE tap), and the reaction mixture was stirred at 25° C. After an appropriate period of time, the resultant homogeneous red solution was absorbed onto silica gel and subjected to column chromatography to furnish the product.

tert-Butyl 3-anilinobutanoylcarbamate (3a). White solid (Et$_2$O:pentane, 1:3, R$_f$ 0.37). Yield >99% (111 mg). m.pt. 117–118° C. HPLC (Chiralpak AD, iPrOH/hexane=2/98, 1.5 mL/min): t$_R$=18.4 min (major) and 23.6 min (minor). [α]$_D^{20}$=–10.4 (c=0.041, CHCl$_3$), 97% ee. $^1$H NMR: 1.30 (d, 3H, CHCH$_3$, $^2J_{HH}$=6.4 Hz); 1.50 (s, 9H, tBu); δ 7.51 (s, br, 1H, CONH); 2.88 (dd, 1H, COCH$_2$, $^1J_{HH}$=6.2 Hz, $^2J_{HH}$=15.9 Hz); 3.08 (dd, 1H, COCH$_2$, $^1J_{HH}$=5.8 Hz, $^2J_{HH}$=15.9 Hz); 3.85 (s, br, 1H, PhNH); 4.03–4.07 (m, 1H, NHCH); 6.62 (d, 2H, Ph, $^2J_{HH}$=8.6 Hz); 6.70 (t, 1H, Ph, $^2J_{HH}$=7.4 Hz); 7.17 (t, 2H, Ph, $^2J_{HH}$=7.4 Hz). $^{13}$C NMR: 20.8 (CH$_3$CH), 27.9 (C(CH$_3$)$_3$), 42.1 (COCH$_2$), 45.9 (NHCH), 82.7 (C(CH$_3$)$_3$), 113.7 (Ph), 117.7 (Ph), 129.3 (Ph), 146.8 (Ph), 150.5 (CO$_2$), 172.8 (COCH$_2$). m/z (HR-ESMS) Expected 278.1630 (M$^+$), observed 278.1625. Anal. calcd for C$_{15}$H$_{22}$N$_2$O$_3$: C, 64.73; H, 7.97; N, 10.06%. Found: C, 64.80; H, 7.77; N, 9.93%.

tert-Butyl 3-[(4-chlorophenyl)amino]butanoylcarbamate (3b). White solid (Et$_2$O:pentane, 1:3, R$_f$ 0.26). Yield >99% (125 mg). m.pt. 114–115° C. HPLC (Chiralpak AD, iPrOH/hexane=2/98, 1.2 mL/min): t$_R$=35.7 min (major) and 41.0 min (minor, located using racemic catalyst). [α]$_D^{20}$=–18.2 (c=0.036, CHCl$_3$), >99% ee. $^1$H NMR: δ 1.28 (d, 3H, CHCH$_3$, $^2J_{HH}$=6.3 Hz); 1.48 (s, 9H, tBu); 2.86 (dd, 1H, COCH$_2$, $^1J_{HH}$=6.0 Hz, $^2J_{HH}$=16.0 Hz); 3.07 (dd, 1H, COCH$_2$, $^1J_{HH}$=5.8 Hz, $^2J_{HH}$=16.0 Hz); 3.89 (s, br, 1H, PhNH); 3.92–4.08 (m, 1H, NHCH); 6.53 (d, 2H, Ph, $^2J_{HH}$=8.8 Hz); 7.10 (d, 2H, Ph, $^2J_{HH}$=8.8 Hz); 7.33 (s, br, 1H, CONH). $^{13}$C NMR: δ 20.7 (CH$_3$CH), 27.9 (C(CH$_3$)$_3$), 41.9 (COCH$_2$), 46.0 (NHCH), 83.8 (C(CH$_3$)$_3$), 115.7 (Ph), 122.1 (Ph), 129.1 (Ph), 145.5 (Ph), 150.6 (CO$_2$), 172.9 (COCH$_2$). m/z (HR-ESMS) Expected 312.1241 (M$^+$), observed 312.1237. Anal. calcd for C$_{15}$H$_{21}$N$_2$O$_3$: C, 57.60; H, 6.77; N, 8.96%. Found: C, 57.58; H, 6.66; N, 8.67%.

tert-Butyl 3-[(4-methylphenyl)amino]butanoylcarbamate (3c). White solid (Et$_2$O:pentane, 1:3, R$_f$ 0.23). Yield 93% (109 mg). m.pt. 84–85° C. HPLC (Chiralpak AD, iPrOH/hexane=2/98, 1.5 mL/min): t$_R$=21.4 min (major) and 25.2 min (minor). [α]$_D^{20}$=–13.6 (c=0.050, CHCl$_3$), 92% ee. $^1$H NMR: δ 1.28 (d, 3H, CHCH$_3$, $^2J_{HH}$=6.4 Hz); 1.48 (s, 9H, tBu); 2.23 (s, 3H, PhCH$_3$); 2.84 (dd, 1H, COCH$_2$, $^1J_{HH}$=6.1 Hz, $^2J_{HH}$=15.9 Hz); 3.02 (dd, 1H, COCH$_2$, $^1J_{HH}$=5.9 Hz, $^2J_{HH}$=15.9 Hz); 3.68 (s, br, 1H, PhNH); 3.96–3.99 (m, 1H, NHCH); 6.56 (d, 2H, Ph, $^2J_{HH}$=8.3 Hz); 6.98 (d, 2H, Ph, $^2J_{HH}$=8.3 Hz); 7.63 (s, br, 1H, CONH). $^{13}$C NMR: δ 20.3 (PhCH$_3$), 20.7 (CH$_3$CH), 27.9 (C(CH$_3$)$_3$), 42.1 (COCH$_2$), 46.3 (NHCH), 82.4 (C(CH$_3$)$_3$), 114.1 (Ph), 127.0 (Ph), 129.7 (Ph), 144.5 (Ph), 150.5 (CO$_2$), 173.0 (COCH$_2$). m/z (HR-ESMS) Expected 292.1787 (M$^+$), observed 292.1766. Anal. calcd for C$_{16}$H$_{24}$N$_2$O$_3$: C, 65.73; H, 8.27; N, 9.58%. Found: C, 65.64; H, 8.43; N, 9.64%.

tert-Butyl 3-[(4-methoxyphenyl)amino]butanoylcarbamate (3d). White solid (Et$_2$O:pentane, 1:1, R$_f$ 0.4). Yield 99% (122 mg). m.pt. 70–71° C. HPLC (Chiralpak AD, iPrOH/hexane=3/97, 1.2 mL/min): t$_R$=30.1 min (major) and 37.8 min (minor). [α]$_D^{20}$=–10.4 (c=0.078, CHCl$_3$), 73% ee. $^1$H NMR: δ 1.26 (d, 3H, CHCH$_3$, $^2J_{HH}$=6.4 Hz); 1.47 (s, 9H, tBu); 2.80 (dd, 1H, COCH$_2$, $^1J_{HH}$=5.8 Hz, $^2J_{HH}$=15.9 Hz); 2.98 (dd, 1H, COCH$_2$, $^1J_{HH}$=5.8 Hz, $^2J_{HH}$=15.9 Hz); 3.50 (s, br, 1H, PhNH); 3.74 (s, 3H, OCH$_3$); 3.88–3.93 (m, 1H, NHCH); 6.61 (d, 2H, Ph, $^2J_{HH}$=8.8 Hz); 6.77 (d, 2H, Ph, $^2J_{HH}$=8.8 Hz); 7.79 (s, br, 1H, CONH). $^{13}$C NMR: δ 20.8 (CH$_3$CH), 27.9 (C(CH$_3$)$_3$), 42.2 (COCH$_2$), 47.3 (NHCH), 55.7 (OCH$_3$), 82.5 (C(CH$_3$)$_3$), 114.9 (Ph), 115.8 (Ph), 140.8 (Ph), 150.4 (CO$_2$), 152.6 (Ph), 172.8 (COCH$_2$). m/z (HR-ESMS) Expected 308.1736 (M$^+$), observed 308.1730. Anal. calcd for C$_{16}$H$_{24}$N$_2$O$_4$: C, 62.32; H, 7.84; N, 9.08%. Found: C, 62.43; H, 7.93; N, 8.86%.

tert-Butyl 3-anilinopentanoylcarbamate (3e). White solid (Et$_2$O:pentane, 1:3, R$_f$ 0.4). Yield 98% (115 mg). m.pt. 105–106° C. HPLC (Chiralpak AD, iPrOH/hexane=2/98, 1.2 mL/min): t$_R$=20.4 min (major) and 24.3 min (minor). [α]$_D^{20}$=–29.0 (c=0.041, CHCl$_3$), 90% ee. $^1$H NMR: δ 0.97 (t, 3H, CH$_2$CH$_3$, $^2J_{HH}$=7.4 Hz); 1.48 (s, 9H, tBu); 1.60–1.72 (m, 2H, CH$_2$CH$_3$); 2.88 (dd, 1H, COCH$_2$, $^1J_{HH}$=5.0 Hz, $^2J_{HH}$=15.4 Hz); 3.01 (dd, 1H, COCH$_2$, $^1J_{HH}$=5.9 Hz, $^2J_{HH}$=15.4 Hz); 3.84 (s, br, 2H, NHCH and PhNH); 6.61 (d, 2H, Ph, $^2J_{HH}$=7.3 Hz); 6.68 (t, 1H, Ph, $^2J_{HH}$=7.3 Hz); 7.15 (t, 2H, Ph, $^2J_{HH}$=7.3 Hz); 7.50 (s, br, 1H, CONH). $^{13}$C NMR: δ 10.4 (CH$_3$CH$_2$), 27.9 (C(CH$_3$)$_3$), 28.0 (CH$_3$CH$_2$), 40.0 (COCH$_2$), 51.7 (NHCH), 82.6 (C(CH$_3$)$_3$), 113.5 (Ph), 117.5 (Ph), 129.3 (Ph), 147.3 (Ph), 150.5 (CO$_2$), 173.0 (COCH$_2$). m/z (HR-ESMS) Expected 292.1787 (M$^+$), observed 292.1781. Anal. calcd for C$_{16}$H$_{24}$N$_2$O$_3$: C, 65.73; H, 8.27; N, 9.58%. Found: C, 65.95; H, 8.12; N, 9.49%.

tert-Butyl 3-[(4-chlorophenyl)amino]pentanoylcarbamate (3f). White solid (Et$_2$O:pentane, 1:2, R$_f$ 0.6). Yield 92% (120 mg). m.pt. 93–94° C. HPLC (Chiralpak AD, iPrOH/hexane=2/98, 1.0 mL/min): t$_R$=32.1 min (major) and 37.3 min (minor). [α]$_D^{20}$=–34.4 (c=0.052, CHCl$_3$), 85% ee. $^1$H NMR: δ 0.96 (t, 3H, CH$_2$CH$_3$, $^2J_{HH}$=7.4 Hz); 1.48 (s, 9H, $^t$Bu); 1.57–1.68 (m, 2H, CH$_2$CH$_3$); 2.88 (dd, 1H, COCH$_2$, $^1J_{HH}$=5.4 Hz, $^2J_{HH}$=15.8 Hz); 3.03 (dd, 1H, COCH$_2$, $^1J_{HH}$=6.2 Hz, $^2J_{HH}$=15.8 Hz); 3.73–3.85 (m, 1H, NHCH); 3.86 (s, br, 1H, PhNH); 6.53 (d, 2H, Ph, $^2J_{HH}$=8.9 Hz); 7.08 (d, 2H, Ph, $^2J_{HH}$=8.9 Hz); 7.33 (s, br, 1H, CONH). $^{13}$C NMR: δ 10.4 (CH$_3$CH$_2$), 27.9 (CH$_3$CH$_2$), 28.0 (C(CH$_3$)$_3$), 40.8 (COCH$_2$), 51.9 (NHCH), 82.8 (C(CH$_3$)$_3$), 114.5 (Ph), 121.8 (Ph), 129.1 (Ph), 145.9 (Ph), 150.5 (CO$_2$), 173.0 (COCH$_2$). m/z (HR-ESMS) Expected 326.1397 (M$^+$), observed 326.1394. Anal. calcd for C$_{16}$H$_{23}$ClN$_2$O$_3$: C, 58.80; H, 7.09; N, 8.57%. Found: C, 59.12; H, 7.04; N, 8.29%.

tert-Butyl 3-[(4-methylphenyl)amino]pentanoylcarbamate (3g). White solid (Et$_2$O:pentane, 1:3, R$_f$ 0.3). Yield 94% (115 mg). m.pt. 96–97° C. The enantiomers cannot be resolved by chiral HPLC. [α]$_D^{20}$=–20.0 (c=0.058, CHCl$_3$). $^1$H NMR: δ 0.96 (t, 3H, CH$_2$CH$_3$, $^2J_{HH}$=7.4 Hz); 1.47 (s, 9H, tBu); 1.57–1.68 (m, 2H, CH$_2$CH$_3$); 2.23 (s, 3H, PhCH$_3$); 2.86 (dd, 1H, COCH$_2$, $^1J_{HH}$=5.3 Hz, $^2J_{HH}$=15.5 Hz); 2.97 (dd, 1H, COCH$_2$, $^1J_{HH}$=6.4 Hz, $^2J_{HH}$=15.5 Hz); 3.69 (s, br, 1H, PhNH); 3.77–3.83 (m, 1H, NHCH); 6.55 (d, 2H, Ph, $^2J_{HH}$=8.4 Hz); 6.97 (d, 2H, Ph, $^2J_{HH}$=8.4 Hz); 7.61 (s, br, 1H, CONH). $^{13}$C NMR (CDCl$_3$): δ 10.4 (CH$_3$CH$_2$), 20.3 (PhCH$_3$), 27.8 (CH$_3$CH$_2$), 27.9 (C(CH$_3$)$_3$), 40.0 (COCH$_2$), 52.1 (NHCH), 82.5 (C(CH$_3$)$_3$), 113.9 (Ph), 126.8 (Ph), 129.8 (Ph), 144.9 (Ph), 150.4 (CO$_2$), 173.0 (COCH$_2$). m/z (HR-ESMS) Expected 306.1943 (M$^+$), observed 306.1938. Anal. calcd for C$_{17}$H$_{26}$N$_2$O$_3$: C, 66.64; H, 8.55; N, 9.14%. Found: C, 66.83; H, 8.68; N, 9.27%.

tert-Butyl 3-[(4-methoxyphenyl)amino]pentanoylcarbamate (3h). White solid (Et$_2$O:pentane, 1:1, R$_f$ 0.6). Yield >99% (128 mg). m.pt. 65–66° C. HPLC (Chiralpak AD, iPrOH/hexane=2/98, 1.2 mL/min): t$_R$=43.9 min (major) and 52.7 min (minor). [α]$_D^{20}$=–5.2 (c=0.067, CHCl$_3$), 16% ee. $^1$H NMR: δ 0.96 (t, 3H, CH$_2$CH$_3$, $^2$J$_{HH}$=7.4 Hz); 1.47 (s, 9H, tBu); 1.58–1.66 (m, 2H, CH$_2$CH$_3$); 2.88 (dd, 1H, COCH$_2$, $^1$J$_{HH}$=5.3 Hz, $^2$J$_{HH}$=15.8 Hz); 2.93 (dd, 1H, COCH$_2$, $^1$J$_{HH}$=6.4 Hz, $^2$J$_{HH}$=15.8 Hz); 3.52 (s, br, 1H, PhNH); 3.69–3.76 (m, 1H, NHCH); 3.73 (s, 3H, OCH$_3$); 6.60 (d, 2H, Ph, $^2$J$_{HH}$=8.6 Hz); 6.76 (d, 2H, Ph, $^2$J$_{HH}$=8.6 Hz); 7.61 (s, br, 1H, CONH). $^{13}$C NMR: δ 10.4 (CH$_3$CH$_2$), 27.7 (CH$_3$CH$_2$), 27.9 (C(CH$_3$)$_3$), 40.0 (COCH$_2$), 53.0 (NHCH), 55.7 (OCH$_3$), 82.5 (C(CH$_3$)$_3$), 114.9 (Ph), 115.4 (Ph), 141.2 (Ph), 150.5 (CO$_2$), 152.4 (Ph), 172.9 (COCH$_2$). m/z (HR-ESMS) Expected 322.1893 (M$^+$), observed 322.1887. Anal. calcd for C$_{17}$H$_{26}$N$_2$O$_4$: C, 63.33; H, 8.13; N, 8.69%. Found: C, 63.47; H, 8.00; N, 8.66%.

tert-Butyl 3-anilinohexanoylcarbamate (3i). White solid (Et$_2$O:pentane, 1:4, R$_f$ 0.3). Yield 98% (120 mg). m.pt. 103–104° C. HPLC (Chiralpak AD, EtOH/hexane=3/97, 1.0 mL/min): t$_R$=15.5 min (major) and 17.5 min (minor). [α]$_D^{20}$=–22.1 (c=0.056, CHCl$_3$), 89% ee. $^1$H NMR: δ 0.92 (t, 3H, CH$_2$CH$_3$, $^2$J$_{HH}$=7.3 Hz); 1.36–1.50 (m, 2H, CH$_2$CH$_3$); 1.47 (s, 9H, tBu); 1.53–1.62 (m, 2H, CH$_2$CH$_2$CH$_3$); 2.89 (dd, 1H, COCH$_2$, $^1$J$_{HH}$=5.5 Hz, $^2$J$_{HH}$=15.9 Hz); 3.00 (dd, 1H, COCH$_2$, $^1$J$_{HH}$=6.4 Hz, $^2$J$_{HH}$=15.9 Hz); 3.81 (s, br, 1H, PhNH); 3.88–3.96 (m, 1H, NHCH); 6.61 (d, 2H, Ph, $^2$J$_{HH}$=7.4 Hz); 6.68 (t, 1H, Ph, $^2$J$_{HH}$=7.4 Hz); 7.15 (t, 2H, Ph, $^2$J$_{HH}$=7.4 Hz); 7.41 (s, br, 1H, CONH). $^{13}$C NMR: δ 14.0 (CH$_3$CH$_2$), 19.3 (CH$_3$CH$_2$), 27.9 (C(CH$_3$)$_3$), 37.5 (CH$_2$CH$_2$CH$_3$), 40.4 (COCH$_2$), 50.0 (NHCH), 82.6 (C(CH$_3$)$_3$), 113.4 (Ph), 117.4 (Ph), 129.3 (Ph), 147.3 (Ph), 150.5 (CO$_2$), 173.0 (COCH$_2$). m/z (HR-ESMS) Expected 306.1943 (M$^+$), observed 306.1938. Anal. calcd for C$_{17}$H$_{26}$N$_2$O$_3$: C, 66.64; H, 8.55; N, 9.14%. Found: C, 66.72; H, 8.49; N, 9.02%.

tert-Butyl 3-[(4-chlorophenyl)amino]hexanoylcarbamate (3j). White solid (Et$_2$O:pentane, 1:4, R$_f$ 0.4). Yield 90% (123 mg). m.pt. 76–77° C. HPLC (Chiralpak AS, iPrOH/hexane=2/98, 1.0 mL/min): t$_R$=20.6 min (major) and 26.2 min (minor). [α]$_D^{20}$=–28.6 (c=0.046, CHCl$_3$), 89% ee. $^1$H NMR: δ 0.91 (t, 3H, CH$_2$CH$_3$, $^2$J$_{HH}$=7.3 Hz); 1.33–1.45 (m, 2H, CH$_2$CH$_3$); 1.48 (s, 9H, tBu); 1.53–1.59 (m, 2H, CH$_2$CH$_2$CH$_3$); 2.88 (dd, 1H, COCH$_2$, $^1$J$_{HH}$=2.6 Hz, $^2$J$_{HH}$=15.4 Hz); 3.02 (dd, 1H, COCH$_2$, $^1$J$_{HH}$=4.8 Hz, $^2$J$_{HH}$=15.4 Hz); 3.85 (s, br, 2H, PhNH, NHCH); 6.52 (d, 2H, Ph, $^2$J$_{HH}$=8.8 Hz); 7.08 (d, 2H, Ph, $^2$J$_{HH}$=8.8 Hz); 7.38 (s, br, 1H, CONH). $^{13}$C NMR: δ 13.9 (CH$_3$CH$_2$), 19.3 (CH$_3$CH$_2$), 27.9 (C(CH$_3$)$_3$), 37.4 (CH$_2$CH$_2$CH$_3$), 40.3 (COCH$_2$), 50.2 (NHCH), 82.7 (C(CH$_3$)$_3$), 114.4 (Ph), 121.8 (Ph), 129.1 (Ph), 146.0 (Ph), 150.5 (CO$_2$), 173.1 (COCH$_2$). m/z (HRMS) Expected 340.1554 (M$^+$), observed 340.1550. Anal. calcd for C$_{17}$H$_{25}$ClN$_2$O$_3$: C, 59.90; H, 7.39; N, 8.22%. Found: C, 60.08; H, 7.14; N, 8.05%.

tert-Butyl 3-[(4-methylphenyl)amino]hexanoylcarbamate (3k). White solid (Et$_2$O:pentane, 1:4, R$_f$ 0.3). Yield 83% (107 mg). m.pt. 63–64° C. HPLC (Chiralpak AS, iPrOH/hexane=1/99, 1.0 mL/min): t$_R$=30.2 min (major) and 27.2 min (minor). [α]D$^{20}$=–21.5 (c=0.052, CHCl$_3$), 80% ee. $^1$H NMR: δ 0.92 (t, 3H, CH$_2$CH$_3$, $^2$J$_{HH}$=7.3 Hz); 1.37–1.50 (m, 2H, CH$_2$CH$_3$); 1.48 (s, 9H, tBu); 1.53–1.61 (m, 2H, CH$_2$CH$_2$CH$_3$); 2.23 (s, 3H, PhCH$_3$); 2.87 (dd, 1H, COCH$_2$, $^1$J$_{HH}$=5.5 Hz, $^2$J$_{HH}$=15.8 Hz); 2.96 (dd, 1H, COCH$_2$, $^1$J$_{HH}$=6.2 Hz, $^2$J$_{HH}$=15.8 Hz); 3.65 (s, br, 1H, PhNH); 3.82–3.90 (m, 1H, NHCH); 6.53 (d, 2H, Ph, $^2$J$_{HH}$=8.4 Hz); 6.97 (d, 2H, Ph, $^2$J$_{HH}$=8.4 Hz); 7.53 (s, br, 1H, CONH). $^{13}$C NMR: δ 14.0 (CH$_3$CH$_2$), 19.3 (CH$_3$CH$_2$), 20.3 (PhCH$_3$), 28.0 (C(CH$_3$)$_3$), 37.4 (CH$_2$CH$_2$CH$_3$), 40.5 (COCH$_2$), 50.5 (NHCH), 82.5 (C(CH$_3$)$_3$), 113.8 (Ph), 126.8 (Ph), 129.8 (Ph), 144.9 (Ph), 150.4 (CO$_2$), 172.9 (COCH$_2$). m/z (HR-ESMS) Expected 320.2100 (M$^+$), observed 320.2095. Anal. calcd for C$_{18}$H$_{28}$N$_2$O$_3$: C, 67.47; H, 8.81; N, 8.74%. Found: C, 67.41; H, 8.97; N, 8.65%.

tert-Butyl 3-[(4-methoxyphenyl)amino]hexanoylcarbamate (3l). Colourless oil (Et$_2$O:pentane, 1:1, R$_f$ 0.6). Yield 82% (110 mg). HPLC (Chiralpak AD, iPrOH/hexane=1.6/98.4, 1.2 mL/min): t$_R$=56.1 min (major) and 62.9 in (minor). [α]$_D^{20}$=–4.2 (c=0.043, CHCl$_3$), 17% ee. $^1$H NMR: δ 0.90 (t, 3H, CH$_2$CH$_3$, $^2$J$_{HH}$=7.2 Hz); 1.34–1.44 (m, 2H, CH$_2$CH$_3$); 1.46 (s, 9H, tBu); 1.49–1.59 (m, 2H, CH$_2$CH$_2$CH$_3$); 2.82 (dd, 1H, COCH$_2$, $^1$J$_{HH}$=5.4 Hz, $^2$J$_{HH}$=15.6 Hz); 2.92 (dd, 1H, COCH$_2$, $^1$J$_{HH}$=6.2 Hz, $^2$J$_{HH}$=15.6 Hz); 3.51 (s, br, 1H, PhNH); 3.72 (s, 3H, OCH$_3$); 3.75–3.81 (m, 1H, NHCH); 6.60 (d, 2H, Ph, $^2$J$_{HH}$=8.9 Hz); 6.75 (d, 2H, Ph, $^2$J$_{HH}$=8.9 Hz); 7.79 (s, br, 1H, CONH). $^{13}$C NMR: δ 14.9 (CH$_3$CH$_2$), 19.3 (CH$_3$CH$_2$), 27.9 (C(CH$_3$)$_3$), 37.3 (CH$_2$CH$_2$CH$_3$), 40.4 (COCH$_2$), 51.4 (NHCH), 55.7 (OCH$_3$), 82.4 (C(CH$_3$)$_3$), 114.9 (Ph), 115.3 (Ph), 141.2 (Ph), 150.4 (CO$_2$), 152.3 (Ph), 173.0 (COCH$_2$). m/z (HR-ESMS) Expected 336.2049 (M$^+$), observed 336.2043. Anal. calcd for C$_{18}$H$_{28}$N$_2$O$_4$: C, 64.26; H, 8.39; N, 8.33%. Found: C, 64.13; H, 8.07; N, 8.15%.

Methyl (2E)-but-2-enoylcarbamate (4). To a mixture of methyl carbamate (1.0 g, 8.54 mmol) and 2-butenoyl chloride (2.4 mL, 25.0 mmol) was added styrene (30 mL), followed by CuCl (0.1 g). The reaction mixture was stirred at 114° C. for 16 h. It was then cooled to room temperature and evaporated to give a white residue, which was dissolved in DCM and washed with water, brine and dried over MgSO$_4$. The solution was concentrated and the addition of pentane to the residue furnished the product as a white precipitate. Yield 76% (0.93 g). m.pt. 149–150° C. $^1$H NMR: δ 1.94 (dd, 1H, CH$_3$CH, $^2$J$_{HH}$=6.8 Hz, $^3$J$_{HH}$=1.4 Hz); 3.78 (s, 3H, OCH$_3$); 6.84 (dd, 1H, COCH, $^2$J$_{HH}$=15.0 Hz, $^3$J$_{HH}$=1.3 Hz); 7.10–7.20 (m, 1H, CH$_3$CH); 7.89 (s, br, 1H, NH). $^{13}$C NMR: δ 18.4 (CH$_3$CH), 53.0 (OCH$_3$), 122.7 (COCH), 146.6 (CH$_3$CH), 152.4 (CO$_2$), 166.1 (COCH). m/z (HR-EIMS) Expected 143.0582 (M$^+$), observed 143.0577. Anal. calcd for C$_9$H$_9$NO$_3$: C, 50.35; H, 6.34; N, 9.79%. Found: C, 50.44; H, 6.59; N, 9.94%.

Methyl 3-anilinobutanoylcarbamate (5). Colourless oil (Et$_2$O:pentane, 1:1, R$_f$ 0.4). Yield 95% (90 mg). HPLC (Chiralpak AD, iPrOH/hexane=5/95, 1.0 mL/min): t$_R$=26.8 min (major) and 33.8 min (minor). [α]$_D^{20}$=–6.5 (c=0.037, CHCl$_3$), 92% ee. $^1$H NMR: δ 1.30 (d, 3H, CHCH$_3$, $^2$J$_{HH}$=6.8 Hz); 2.89 (dd, 1H, COCH$_2$, $^1$J$_{HH}$=5.9 Hz, $^2$J$_{HH}$=15.9 Hz); 3.05 (dd, 1H, COCH$_2$, $^1$J$_{HH}$=5.9 Hz, $^2$J$_{HH}$=15.9 Hz); 3.76 (s, 4H, 1H, PhNH, 3H, OCH$_3$); 3.99–4.08 (m, 1H, NHCH); 6.64 (d, 2H, Ph, $^2$J$_{HH}$=7.7 Hz); 6.72 (t, 1H, Ph, $^2$J$_{HH}$=7.3 Hz); 7.18 (t, 2H, Ph, $^2$J$_{HH}$=7.3 Hz); 7.72 (s, br, 1H, CONH). $^{13}$C NMR: δ 20.8 (CH$_3$CH), 42.2 (COCH$_2$), 46.0 (NHCH), 53.0 (OCH$_3$), 113.9 (Ph), 118.0 (Ph), 129.3 (Ph), 146.7 (Ph), 152.2 (CO$_2$), 172.5 (COCH$_2$). m/z (HR-ESMS) Expected 236.1161 (M$^+$), observed 236.1155. Anal. calcd for C$_{12}$H$_{16}$N$_2$O$_3$: C, 61.00; H, 6.83; N, 11.86%. Found: C, 59.95; H, 6.60; N, 11.47%.

Deprotection of compound 3a to β-amino acid 6: Compound (−)-3a (0.10 g, 0.36 mmol, 90% ee) was hydrolysed with 1N KOH in MeOH (2.5 eqiv.) at room temperature for 1 h, after which the reaction mixture was evaporated. The residue was then dissolved in water, and washed with portions of Et$_2$O. The aqueous phase was acidified with 1N HCl (pH 4), before extracting with EtOAc (4×10 mL). The combined organic layers were washed with brine, dried over MgSO$_4$ and evaporated to afford β-amino acid 6 quantitatively (64 mg). $[\alpha]_D^{20}$ =+18.1 (c=0.032, CHCl$_3$). $^1$H NMR: δ 1.29 (d, 3H, CHCH$_3$, $^2J_{HH}$=6.4 Hz); 2.51 (dd, 1H, COCH$_2$, $^1J_{HH}$=6.4 Hz, $^2J_{HH}$=15.4 Hz); 2.66 (dd, 1H, COCH$_2$, $^1J_{HH}$=5.9 Hz, $^2J_{HH}$=15.4 Hz); 3.89–3.98 (m, 1H, CH$_3$CH); 6.30 (s, br, 2H, CHNH and COOH); 6.68 (d, 2H, Ph, $^2J_{HH}$=7.8 Hz); 6.78 (t, 1H, Ph, $^2J_{HH}$=7.4 Hz); 7.21 (t, 2H, Ph, $^2J_{HH}$=7.4 Hz). $^{13}$C NMR: δ 20.6 (CH$_3$CH), 40.6 (COCH$_2$), 46.5 (NHCH), 114.5 (Ph), 118.7 (Ph), 129.4 (Ph), 146.1 (Ph), 176.6 (CO$_2$H). m/z (HR-EIMS) Expected 179.0946 (M$^+$), observed 179.0941.

Deprotection of compound 3a to β-amino amide 7: Compound (−)-3a (0.10 g, 0.37 mmol, 94% ee) was dissolved in a 1:1 mixture of CH$_2$Cl$_2$ and TFA (2 mL). The mixture was stirred at room temperature for 1 h and then evaporated in vacuo. The residue was purified by chromatography (EtOAc:Et$_3$N=50:1) to give the pure amide 7 quantitatively, 66 mg. $[\alpha]^{20}_D$=+37.4 (c=0.033, CHCl$_3$). $^1$H NMR (CDCl$_3$): δ 1.29 (d, 3H, CHCH$_3$, $^2J_{HH}$=6.4 Hz); 2.39 (dd, 1H, COCH$_2$, $^1J_{HH}$=5.5 Hz, $^2J_{HH}$=15.0 Hz); 2.48 (dd, 1H, COCH$_2$, $^1J_{HH}$=6.4 Hz, $^2J_{HH}$=15.0 Hz); 3.73 (s, br, 1H, PhNH); 3.88–3.96 (m, 1H, CH$_3$CH); 5.60 (s, br, 1H, CONH$_2$); 6.03 (s, br, 1H, CONH$_2$); 6.66 (d, 2H, Ph, $^2J_{HH}$=7.8 Hz); 6.75 (t, 1H, Ph, $^2J_{HH}$=7.3 Hz); 7.19 (t, 2H, Ph, $^2J_{HH}$=7.3 Hz). $^{13}$C NMR (CDCl$_3$): δ 20.8 (CH$_3$CH), 42.1 (COCH$_2$), 46.6 (NHCH), 114.1 (Ph), 118.3 (Ph), 129.4 (Ph), 146.7 (Ph), 173.5 (CONH$_2$). m/z (HR-EIMS) Expected 178.1106 (M$^+$), observed 178.1101. Anal. calcd for C$_{10}$H$_{14}$N$_2$O: C, 67.39; H, 7.92; N, 15.72%. Found: C, 67.23; H, 8.07; N, 15.90%.

TABLE 1

Addition of aryl amines to N-alkenoyl carbamates.[a]

| entry | R | Y | Prod | [Pd]/mol % | T/h | Yield (%)[b] | Ee[c]/% |
|---|---|---|---|---|---|---|---|
| 1 | Me | H | 3a | 5 | 18 | >99 | 97 |
| 2 | Me | H | 3a | 5 | 40 | 94 | 94[d] |
| 3 | Me | H | 3a | 2 | 40 | >99 | 92 |
| 4 | Me | Cl | 3b | 5 | 18 | >99 | >99 |
| 5 | Me | Cl | 3b | 2 | 18 | >99 | >99 |
| 6 | Me | Me | 3c | 5 | 18 | 93 | 92 |
| 7 | Me | OMe | 3d | 5 | 40 | 99 | 73 |
| 8 | Et | H | 3e | 5 | 72 | 98 | 90 |
| 9 | Et | Cl | 3f | 5 | 72 | 92 | 85 |
| 10 | Et | Me | 3g | 5 | 120 | 94 | —[e] |
| 11 | Et | OMe | 3h | 5 | 72 | >99 | 16 |
| 12 | $^n$Pr | H | 3i | 5 | 120 | 98 | 89 |
| 13 | $^n$Pr | Cl | 3j | 5 | 120 | 90 | 89 |
| 14 | $^n$Pr | Me | 3k | 5 | 120 | 83 | 80 |
| 15 | $^n$Pr | OMe | 3l | 5 | 120 | 82 | 17 |

[a]Unless otherwise indicated, reactions were performed using 1 equiv of amine and 1.5 equiv of carbamate ester in toluene at 25° C.
[b]Isolated yield following column chromatography.
[c]Determined by chiral HPLC.
[d]in CH2Cl2.
[e]Unresolved (sample is optically active).

The invention claimed is:

1. A process for forming a compound of formula I

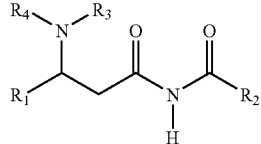

comprising reacting a compound of formula II

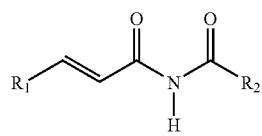

with a compound of formula III

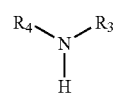

in the presence of the catalyst [(R-BINAP)Pd(solvent)$_2$]$^{2+}$ [TfO]$^−_2$ wherein
  $R_1$ is selected from the group consisting of:
    (a) a peptide, an amino acid, a dipeptide, a sugar, and a polymer; and
    (b) H, C$_{1-12}$ alkyl, C$_{2-12}$ alkenyl, C$_{2-12}$ alkynyl C$_{3-12}$ aryl and C$_{3-12}$ heterocyclyl;
    which is optionally substituted by one or more of C$_{1-6}$ alkyl, halogen, C$_{1-6}$ haloalkyl, OR$_5$, SR$_5$, NO$_2$, CN, NR$_5$R$_5$, NR$_5$COR$_5$, NR$_5$CONR$_5$R$_5$, NR$_5$COR$_5$, NR$_5$CO$_2$R$_5$, CO$_2$R$_5$, COR$_5$, CONR$_{52}$, S(O)$_2$R$_5$, SONR$_{52}$, S(O)R$_5$, SO$_2$NR$_5$R$_5$, NR$_5$S(O)$_2$R$_5$; wherein each R$_5$ is individually selected from hydrogen, C$_{1-6}$ alkyl, C$_{1-6}$ haloalkyl and C$_{6-12}$ aryl;
  $R_2$ is hydrogen, C$_{1-12}$ alkyl, or aryl or with the adjacent carboxyl group forms an amino protecting group such as a carbamate including benzyloxycarbonyl, t-butoxycarbonyl, 2-(4-biphenylyl)-isopropoxycarbonyl, 9-fluorenylmethoxycarbonyl, wherein said alkyl or aryl group can be optionally substituted with one or more of those groups selected from C$_{1-6}$ alkyl, halogen, C$_{1-6}$ haloalkyl, OR$_5$, SR$_5$, NO$_2$, CN, NR$_5$R$_5$, NR$_5$COR$_5$, NR$_5$CONR$_5$R$_5$, NR$_5$COR$_5$, NR$_5$CO$_2$R$_5$, CO$_2$R$_5$, COR$_5$, CONR$_{52}$, S(O)$_2$R$_5$, SONR$_{52}$, S(O)R$_5$, SO$_2$NR$_5$R$_5$, NR$_5$S(O)$_2$R$_5$, wherein the C$_{1-12}$ alkyl group optionally incorporates one or two insertions selected from the group consisting of —O—, —N(R$_5$)—, —S(O)— and —S(O$_2$)—, wherein each R$_5$ is the same or different;
  $R_3$ is H or C$_{1-12}$ alkyl;
  $R_4$ is aryl or heterocycyl, wherein the aryl or heteroaryl group is optionally substituted with one or more of the groups described for R$_2$; and
  $R_5$ is hydrogen, C$_{1-6}$ alkyl, C$_{1-6}$ haloalkyl or C$_{6-12}$ aryl.

2. The process of claim 1, wherein R$_1$ is a C$_{1-10}$ alkyl group.

3. The process of claim 2, wherein $R_1$ methyl, ethyl or n-propyl.

4. The process of claim 1, wherein $R_2$ is $OCH_3$ or $OC(CH_3)_3$.

5. The process of claim 1, wherein $R_3$ is H.

6. The process of claim 1, wherein $R_4$ is

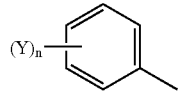

wherein Y is H, halogen, $C_{1-6}$ alkyl or $OC_{1-6}$ alkyl; and n is 1 to 5.

7. The process of claim 6 wherein Y is H, Cl, methyl or O-methyl.

8. The process of claim 1, further comprising the step of:
(a) transforming the compound of Formula I under mild basic conditions to a β-amino acid; or
(b) transforming the compound of Formula I under mild acidic conditions to a β-amino amide.

9. The process of claim 1, wherein the catalyst is provided at 2–5 mol%.

10. The process of claim 1, wherein the solvent is toluene.

11. The process of claim 1, wherein the solvent is dichloromethane or acetonitrile.

12. The process of claim 1, wherein $R_1$ is a peptide, an amino acid, a dipeptide, a sugar, or a polymer.

13. The process of claim 1, wherein $R_1$ is H, $C_{1-12}$ alkyl, $C_{2-12}$ alkenyl, $C_{2-12}$ alkynyl, $C_{3-12}$ aryl or $C_{3-12}$ heterocyclyl; which is optionally substituted by one or more of $C_{1-6}$ alkyl, halogen, $C_{1-6}$ haloalkyl, $OR_5$, $SR_5$, $NO_2$, CN, $NR_5R_5$, $NR_5COR_5$, $NR_5CONR_5$ $R_5$, $NR_5COR_5$, $NR_5CO_2R_5$, $CO_2R_5$, $COR_5$, $CONR_{52}$, $S(O)_2R_5$, $SONR_{52}$, $S(O)R_5$, $SO_2NR_5R_5$, $NR_5S(O)_2R_5$; wherein each R5 is individually selected from hydrogen, $C_{1-6}$ alkyl, $C_{1-6}$ haloalkyl and $C_{6-12}$ aryl.

* * * * *